United States Patent [19]

Smith et al.

[11] Patent Number: 4,859,180
[45] Date of Patent: Aug. 22, 1989

[54] SELF-DRYING CHEEK RETRACTING MIRROR

[76] Inventors: Roderick J. Smith, 2900 Moss St., Lafayette, La. 70501; Leopold A. Castille, Rte. 7, Box 17 E15, Opelousas, La. 70570

[21] Appl. No.: 214,124

[22] Filed: Jun. 30, 1988

[51] Int. Cl.$^4$ ............................ A61C 1/00; A61C 3/00
[52] U.S. Cl. ........................................ 433/31; 433/136
[58] Field of Search ............................ 433/136, 30, 31

[56] References Cited

U.S. PATENT DOCUMENTS

| | | | |
|---|---|---|---|
| 1,157,565 | 10/1915 | Mayer | 433/31 |
| 2,574,217 | 11/1951 | Lundgren et al. | 433/31 |
| 3,631,598 | 1/1972 | Lussier | 433/31 |

*Primary Examiner*—Robert Peshock
*Attorney, Agent, or Firm*—John F. Sieberth

[57] ABSTRACT

Dental mirrors are described that by virtue of their design and configuration are self-drying and have the capability of retracting the cheek away from the teeth being examined or worked on by the dentist, all with comfort for and safety to the patient. The mirrors have clips or the like to detachably secure an absorbent roll thereon. The absorbent roll, such as a cotton roll commonly used in the practice of dentistry for absorbing fluids from various regions of the mouth, is preferably positioned and secured in a substantially tangential position relative to a circular or elliptically-shaped mirror. This tangential position in turn may be varied relative to the longitudinal axis of the elongate handle of the dental mirror, since the mirrors can be used for viewing and absorbing fluids from any region of the mouth. Such mirrors enable the dentist to retract the gum from the gumline by means of a soft absorbent roll rather than a hard surface such as the rim of a dental mirror which can and does cause discomfort and even injury to the patient. Concurrently the fluids in the vicinity of the absorbent roll are readily absorbed. Since the roll is in close proximity to the face of the mirror, this absorptive action in turn tends to keep the face of mirror 15 free or at least freer of fluids which would otherwise accumulate thereon. Consequently the ability of the dentist to view the area being examined or worked on is enhanced. Also, with properly designed clips it is a simple matter to replace wet rolls with fresh, dry rolls as needed during the examination or treatment being performed.

18 Claims, 3 Drawing Sheets

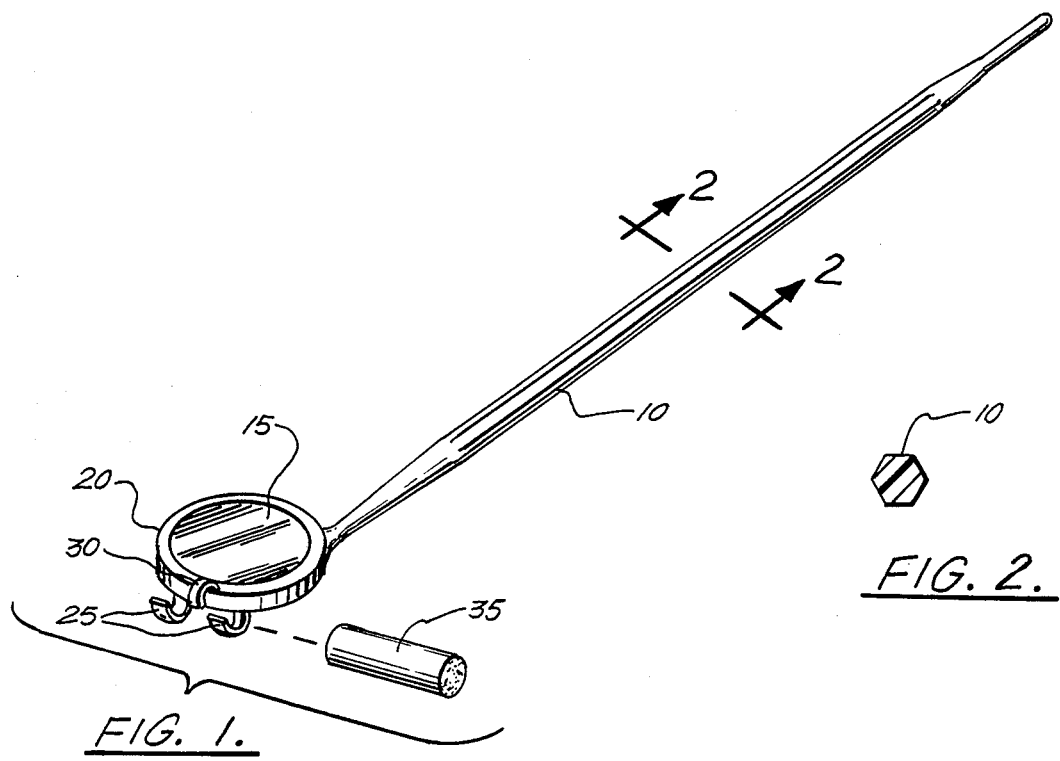
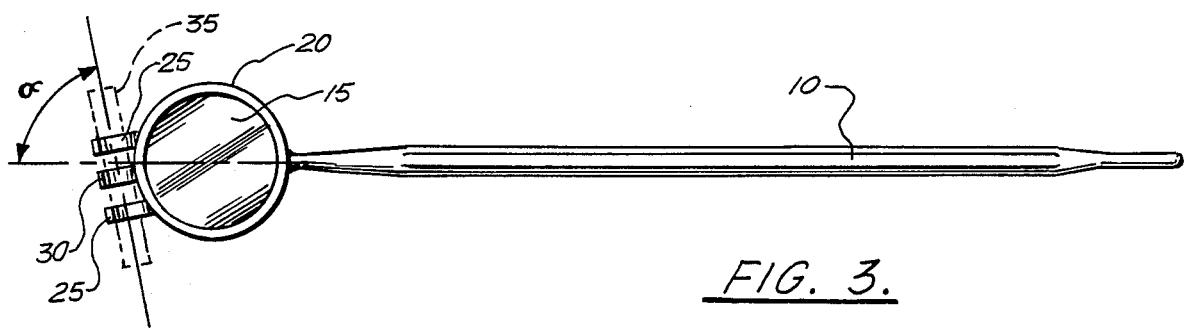
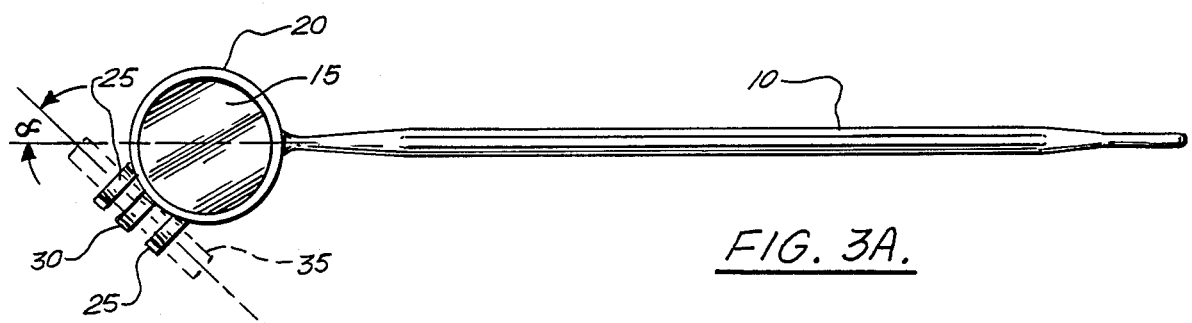

4,859,180

SELF-DRYING CHEEK RETRACTING MIRROR

TECHNICAL FIELD

This invention relates in general to dental mirrors and more particularly to dental mirrors that by virtue of their design and configuration are self-drying and have the capability of retracting the cheek away from the teeth being examined or worked on by the dentist, all with comfort for and safety to the patient.

BACKGROUND

As is well known, dental mirrors are employed by the dentist to enable the areas of the teeth being examined or worked on to be seen by the dentist. Areas that are particularly difficult to see and to work on are the areas between the rear molars and the patient's cheek because of the relatively close spacing that exists between them. It has been proposed heretofore to provide a oversized dental mirror in order to push the cheek away from the gums in the region of the large molars. However this is often quite uncomfortable for the patient and can result in injury to the mouth in the vicinity of the gums or cheek.

A problem with present-day dental mirrors is that they tend to become drenched with saliva and other fluids making it difficult for the dentist to see the area under surveillance.

THE INVENTION

This invention provides an efficient way of overcoming the problems of retracting the cheek from the gums, both safely and comfortably for the patient, and at the same time minimizing the problems created by fluids accumulating on the face of the mirror during use. Indeed, this invention also makes it possible for the dentist to dry out various areas in the patient's mouth rapidly without use of an aspirator or other specialized equipment.

In accordance with one embodiment of this invention there is provided a dental mirror having means adapted to detachably secure an absorbent roll thereon. The absorbent roll, such as a cotton roll commonly used in the practice of dentistry for absorbing fluids from various regions of the mouth, is preferably positioned and secured in a substantially tangential position relative to a circular or elliptically-shaped mirror. This tangential position in turn may be varied relative to the longitudinal axis of the elongate handle of the dental mirror, since the improved mirrors of this invention can be used for viewing and absorbing fluids from any region of the mouth. Moreover the mirrors of this invention can be especially adapted for use either by left-handed dentists or by right-handed dentists and in this case the most desirable positions may differ relative to the axis of the handle. However in preferred embodiments the means for holding the roll in place on the mirror will be positioned such that the roll will retract the cheek when the mirror is disposed in a viewing position in proximity to the outer side of the gumline, especially when in position to view the outer sides of molars numbers 1–3, 14–16, 17–19 and 30–32.

The means for detachably attaching the absorbent roll to the mirror can be varied, but preferably are composed of a plurality of arcuate clips adapted to grip and detachably secure the roll in the desired position relative to the mirror and the mirror handle. For best results the clips should be relatively narrow in width, with one such clip positioned to grip the roll on one side in the vicinity of the midpoint of its length and two such clips spaced apart and positioned to grip the roll in separate places on its side opposite to that being gripped by the first clip.

Thus in its preferred forms this invention provides a distinct and marked improvement in dental mirrors composed of an elongate handle and a mirror angularly disposed from one end of the handle, which improvement involves the provision and utilization of means integral with the dental mirror for detachably securing an absorbent roll in proximity to the periphery of the rimmed mirror.

In another of its embodiments this invention provides a method which involves concurrently retracting the gum from the gumline and absorbing fluids in proximity to said gumline, which method comprises inserting between said gum and said gumline a dental mirror having affixed thereto an absorbent roll so that said absorbent roll effects such retraction and absorption. This method offers the dentist an improved opportunity to observe the area in the mouth where the retraction and absorption are being effected, since the absorbent roll tends to reduce the extent to which the viewing surface of the mirror would otherwise become drenched with fluids.

The above and other features and embodiments of this invention will be still further apparent from the ensuing description, appended claims and accompanying drawings.

THE DRAWINGS

FIG. 1 is a view in perspective of a mirror of this invention with the reflective face of the mirror visible;

FIG. 2 is a cross section of the handle of the mirror of FIG. 1 taken along line 2,2 of FIG. 1;

FIG. 3 is a top view (i.e., looking down toward the reflective face) of a mirror of this invention with the means for securing the roll located to the front side of the mirror (i.e., remote from the handle) and offset from the longitudinal axis of the handle;

FIG. 3A is a top view (i.e., looking down toward the reflective face) of a mirror of this invention with the means for securing the roll located to the front side of the mirror (i.e., remote from the handle) and offset from the longitudinal axis of the handle by a greater amount than the mirror of FIG. 3;

DESCRIPTION OF PREFERRED EMBODIMENTS

Figure 5:
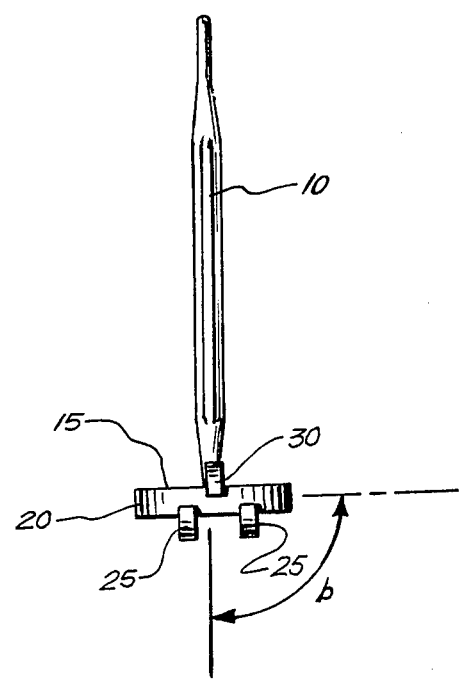
FIG. 5 is a frontal view of a mirror such as depicted in FIG. 3 with the face of the mirror facing upwardly.
Figure 6:
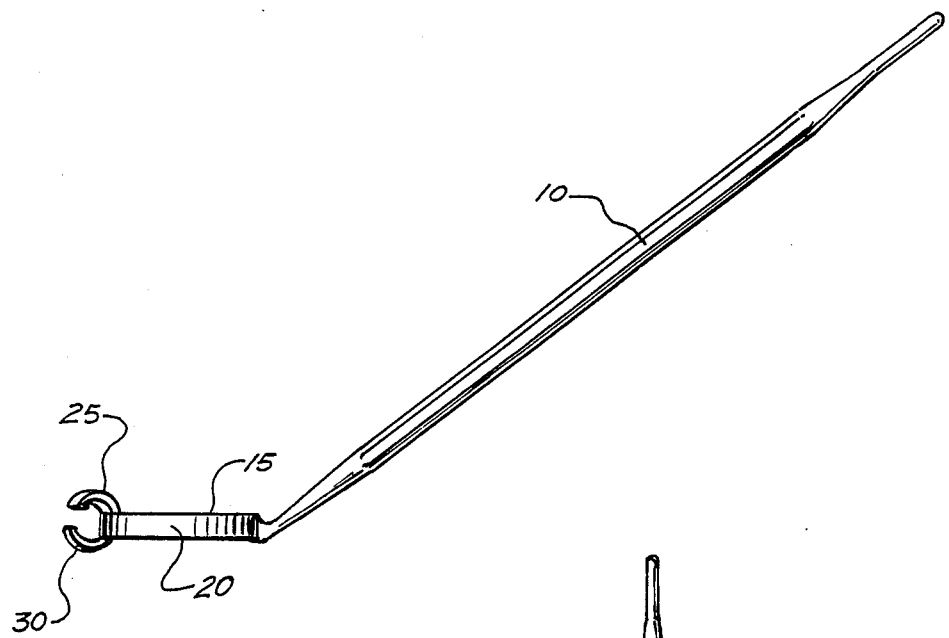
FIG. 6 is a side view of a mirror such as depicted in FIG. 3 with the face of the mirror facing upwardly, but with the clamps in inverted position as compared to the clamps in FIG. 3.
Figure 7:
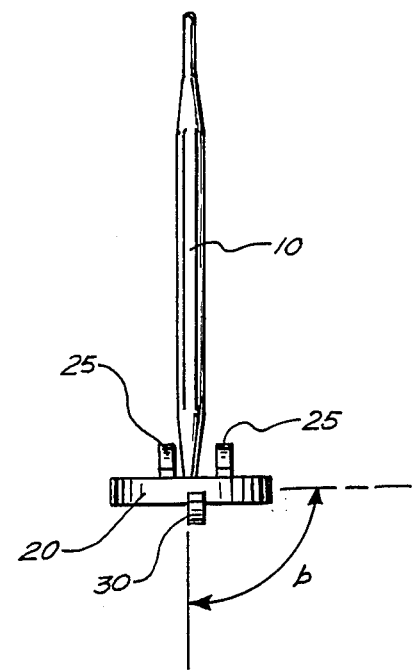
FIG. 7 is a frontal view of a mirror such as depicted in FIG. 6 with the face of the mirror facing upwardly.

Referring to the Figures, wherein like numerals represent like parts among the several views, the dental mirrors of this invention in the forms depicted include an elongate handle 10, and a reflective mirror 15 secured to one end of handle 10 by means of backing 20. As is customary and as depicted in FIG. 6, the face of mirror 15 and its backing 20 are angularly disposed relative to handle 10 so that the face of mirror 15 occupies a plane disposed less than 180 degrees from the plane occupied by the handle. As indicated in FIGS. 5 and 7, the mirror and its backing may be canted to one side so that angle b is somewhat more or somewhat less than 90 degrees. As depicted, mirror 15 and backing 20 are circular in configuration but they may be elliptical or polygonal, or of any other useable shape for a dental mirror. The handle and backing may be made of metal or ceramic materials but preferably are composed of a high temperature resistant plastic. The face of the mirror may be made of glass or transparent plastic material or a highly reflective metallic surface. Handle 10 may be hexagonal in cross section (note FIG. 2) or it may have a round, square, or other polygonal cross section.

Often the backing for mirror 15 will extend over the edge of the facial (front) side of the mirror (as depicted). However it is possible to eliminate the rim around the mirror and secure the mirror portion to the backing by means of a suitable fluid-resistant adhesive.

In the forms depicted, an absorbent roll 35, such as a standard dental cotton roll, can be detachably secured to the perimeter of backing 20 by means of a plurality of arcuate clips 25,25,30. These clips are preferably made from a plastic material that possesses adequate resiliency and flexing strength to enable repeated insertion and removal of rolls 35 during the lifetime of the mirror. While the number and relative positions of the clips may be varied to suit the needs of the occasion, in the preferred form depicted in FIGS. 1, 3, 3A, 4, and 5, clip 30 grasps roll 35 on and around a portion of its upper side and clips 25,25 grasp the roll on and around a portion of its lower side. Conversely, in the form depicted in FIGS. 6 and 7 clip 30 grasps roll 35 on and around a portion of its lower side and clips 25,25 grasp the roll on and around a portion of its upper side. In either case, clip 30 grips the roll at about its midpoint in length whereas clips 25,25 grip the roll at respective spaced-apart loci intermediate the midpoint and the respective ends of the roll. If desired, additional clips or wider clips may be employed. The use of but two opposed clips is also feasible. The chief requirements are that the clips suitably secure roll 35 in the desired position, allow roll 35 to be interposed between the teeth and the cheek and between the gumline and the cheek without causing injury or discomfort to the patient, and present a sufficient amount of exposed roll surfaces to enable the roll to perform its absorptive function in an efficient manner. To this end, the clips preferably compress the roll at the gripping locations so that the adjacent exposed portions of the roll tend to be larger in circumference by virtue of such squeezing action.

Figure 4:
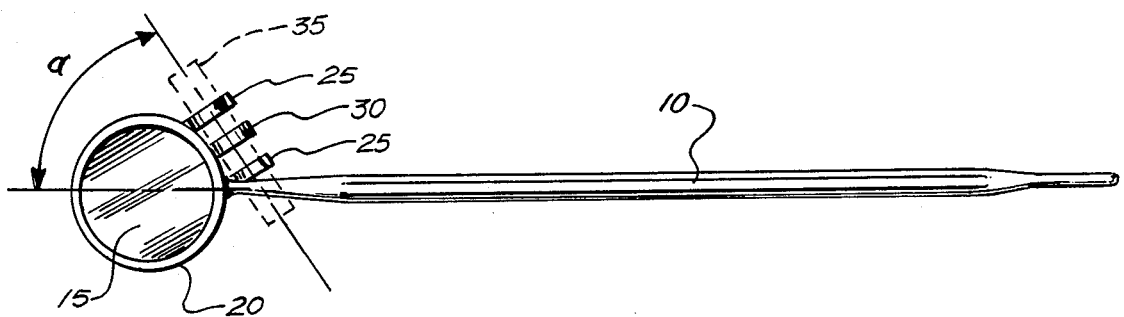
FIG. 4 is a top view (i.e., looking down toward the reflective face) of another mirror of this invention with the means for securing the roll located to the rear side of the mirror (i.e., proximate to the handle) and offset from the longitudinal axis of the handle.

As noted above, the positioning of the means for securing the roll 35 near the perimeter of mirror 15 or backing 20—in this case clips 25,25,30—can be varied. Thus as shown in FIGS. 1, 3, 3A, 5, 6, and 7, the roll may be detachably secured near the front side of the mirror (i.e., remote from handle 10) and as shown in FIGS. 3 and 3A, may be offset from the longitudinal axis of the handle to any desired extent. Hence angle alpha in FIGS. 3 and 3A may be varied anywhere between zero and 90 degrees, although in most cases angle alpha will fall in the range of 25 to 70 degrees. Angle alpha may of course be on the other side of the axis of handle 10 so that roll 35 is offset above the axis depicted in FIGS. 3 and 3A. Similarly, FIG. 4 illustrates the fact that roll 35 may be detachably secured near the rear side of the mirror (i.e., proximate to handle 10) and offset from the longitudinal axis of the handle to any desired extent. Thus angle alpha in FIG. 4 may be varied, again anywhere between zero and 90 degrees and be on either side of the axis of the handle. In most cases angle alpha in FIG. 4 will fall in the range of 5 to 20 degrees.

It will be seen from the foregoing that the use of the improved mirrors of this invention enables the dentist to retract the gum from the gumline by means of a soft absorbent roll 35 rather than a hard surface such as the rim of a dental mirror which can and does cause discomfort and even injury to the patient. Concurrently the fluids in the vicinity of the absorbent roll are readily absorbed. Since roll 35 is in close proximity to the face of mirror 15, this absorptive action in turn tends to keep the face of mirror 15 free or at least freer of fluids which would otherwise accumulate thereon. Consequently the ability of the dentist to view the area being examined or worked on is enhanced. Moreover, with properly designed clips or other roll-securing means it is a simple matter to replace wet rolls with fresh, dry rolls as needed during the examination or treatment being performed.

Additional advantages of the mirror constructions of this invention include their relatively low cost and ease of manufacture by commonly used technology such as injection molding and the like.

The mirrors of this invention may be fabricated from separate parts suitably united by adhesives, by threaded connections, by connections that fit together by snapping action, or the like. Alternatively, the mirrors of this invention may be totally or almost totally formed as integral units, produced for example by appropriate molding procedures.

This invention is not intended to be unduly limited by the foregoing description, as the invention is susceptible to considerable variation in its practice within the spirit and scope of the ensuing claims.

We claim:

1. A dental mirror comprising an elongate handle, a mirror angularly disposed from one end of said handle, and means adapted to detachably secure an absorbent roll in a substantially linear and tangential position relative to the periphery of the mirror such that said roll retracts the cheek when said mirror is disposed in a viewing position in proximity to the outer side of a gumline.

2. An article according to claim 1 wherein said means is still further adapted to secure said roll in a position to retract the cheek when said mirror is disposed in proximity to the outer side of the gumline normally adjacent molars number 1 to 3.

3. An article according to claim 1 wherein said means is still further adapted to secure said roll in a position to retract the cheek when said mirror is disposed in proximity to the outer side of the gumline normally adjacent molars number 14 to 16.

4. An article according to claim 1 wherein said means is still further adapted to secure said roll in a position to retract the cheek when said mirror is disposed in proximity to the outer side of the gumline normally adjacent molars number 17 to 19.

5. An article according to claim 1 wherein said means is still further adapted to secure said roll in a position to retract the cheek when said mirror is disposed in proximity to the outer side of the gumline normally adjacent molars number 30 to 32.

6. An article according to claim 1 wherein said means comprises a plurality of arcuate clips adapted to grip and detachably secure said roll in said position.

7. An article according to claim 6 wherein said clips are composed of a plastic material capable of gripping said roll by a flexing action.

8. An article according to claim 6 wherein said clips are positioned and adapted to grip said roll around portions of opposite sides thereof.

9. An article according to claim 8 wherein said clips are composed of a plastic material capable of gripping said roll by a flexing action.

10. An article according to claim 6 wherein said clips are relatively narrow in width and one such clip is positioned to grip said roll on one side in the vicinity of the midpoint of its length and two such clips are in spaced-apart position to grip said roll on its opposite side in separate positions intermediate said midpoint and the respective ends of the roll.

11. An article according to claim 10 wherein said clips are composed of a plastic material capable of gripping said roll by a flexing action.

12. In a dental mirror comprising an elongate handle and a mirror angularly disposed from one end of said handle, the improvement which comprises means integral with said dental mirror for detachably securing an absorbent roll in proximity to the periphery of the mirror.

13. An article of claim 12 wherein said means comprises a plurality of arcuate clips adapted to detachably secure the roll from a peripheral portion of the mirror remote from the end of the handle from which the mirror is angularly disposed.

14. An article of claim 13 wherein the mirror is essentially circular and wherein said clips are adapted to secure the roll in a position essentially tangential to the mirror and angularly disposed from the longitudinal axis of said handle.

15. An article of claim 14 wherein said clips are composed of a plastic material capable of gripping said roll by a flexing action.

16. An article of claim 12 wherein said means comprises a plurality of arcuate clips adapted to detachably secure the roll from a peripheral portion of the mirror proximate to the end of the handle from which the mirror is angularly disposed.

17. An article of claim 16 wherein the mirror is essentially circular and wherein said clips are adapted to secure the roll in a position essentially tangential to the mirror and angularly disposed from the longitudinal axis of said handle.

18. An article of claim 17 wherein said clips are composed of a plastic material capable of gripping said roll by a flexing action.

* * * * *